United States Patent
Van Schalkwyk et al.

(10) Patent No.: US 10,188,825 B2
(45) Date of Patent: Jan. 29, 2019

(54) HUMIDIFIER FOR A RESPIRATORY ASSISTANCE DEVICE, A RESPIRATORY ASSISTANCE DEVICE AND RELATED METHODS AND APPARATUS

(71) Applicant: Fisher & Paykel Healthcare Limited, Auckland (NZ)

(72) Inventors: Andre Van Schalkwyk, Auckland (NZ); Anthony James Newland, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 478 days.

(21) Appl. No.: 14/776,265

(22) PCT Filed: Mar. 11, 2014

(86) PCT No.: PCT/NZ2014/000033
§ 371 (c)(1),
(2) Date: Sep. 14, 2015

(87) PCT Pub. No.: WO2014/142674
PCT Pub. Date: Sep. 18, 2014

(65) Prior Publication Data
US 2016/0045704 A1    Feb. 18, 2016

Related U.S. Application Data

(60) Provisional application No. 61/782,146, filed on Mar. 14, 2013.

(51) Int. Cl.
*A61M 16/00* (2006.01)
*A61M 16/16* (2006.01)
(Continued)

(52) U.S. Cl.
CPC ........ *A61M 16/16* (2013.01); *A61M 16/0875* (2013.01); *A61M 16/109* (2014.02);
(Continued)

(58) Field of Classification Search
CPC .............. A61M 16/16; A61M 16/0875; A61M 16/1075; A61M 2205/368;
(Continued)

(56) References Cited

U.S. PATENT DOCUMENTS 7,958,891 B2    6/2011  Smith et al.
2007/0230927 A1  10/2007  Kramer
(Continued)

FOREIGN PATENT DOCUMENTS

CN    202613662 U    12/2012
WO    WO 2012/164407 A1    12/2012

OTHER PUBLICATIONS

Neuman, O. et al., Solar Vapor Generation Enabled by Nanoparticles, ACS NANO, 2013, vol. 7(1) 42-49.
(Continued)

*Primary Examiner* — Steven Douglas
(74) *Attorney, Agent, or Firm* — Knobbe, Martens, Olson & Bear, LLP

(57) ABSTRACT

A humidifier for a respiratory assistance device, is provided wherein at least a portion of an inside of a chamber is exposed to light such that light impinges on a metallic or carbon-based material to generate localized heating of liquid molecules around the metallic or carbon-based material and generate vapour for use by the respiratory assistance device. A respiratory assistance device comprising a humidifier and related methods and apparatus are also provided. Arrangements are provided for generating vapour by impinging light on metallic and/or carbon based material, particularly in the form of nanoparticles.

20 Claims, 3 Drawing Sheets

(51) Int. Cl.
*A61M 16/08* (2006.01)
*H05B 3/00* (2006.01)
*H05B 3/14* (2006.01)
*H05B 3/54* (2006.01)
*A61M 16/10* (2006.01)

(52) U.S. Cl.
CPC .... *A61M 16/1075* (2013.01); *A61M 16/1095* (2014.02); *H05B 3/0085* (2013.01); *H05B 3/145* (2013.01); *H05B 3/54* (2013.01); *A61M 16/108* (2014.02); *A61M 16/1085* (2014.02); *A61M 2205/0244* (2013.01); *A61M 2205/3368* (2013.01); *A61M 2205/368* (2013.01); *A61M 2205/584* (2013.01); *A61M 2205/7545* (2013.01); *H05B 2203/021* (2013.01); *H05B 2203/022* (2013.01); *H05B 2214/04* (2013.01)

(58) Field of Classification Search
CPC .. A61M 2205/0244; A61M 2205/3368; A61M 2205/584; A61M 2205/7545; A61M 16/108; A61M 16/1085; A61M 16/109; A61M 16/1095; H05B 3/0085; H05B 3/145; H05B 3/54; H05B 2203/021; H05B 2203/022; H05B 2214/04
See application file for complete search history.

(56) References Cited

U.S. PATENT DOCUMENTS

| 2008/0032119 | A1* | 2/2008 | Feldhahn | A61M 16/06 428/332 |
| 2010/0243432 | A1* | 9/2010 | Ikemizu | F24F 6/043 204/196.37 |
| 2012/0184941 | A1 | 7/2012 | Levy et al. | |
| 2013/0081621 | A1* | 4/2013 | Korneff | A61M 16/16 128/203.27 |
| 2016/0200179 | A1* | 7/2016 | Kim | B60H 3/022 62/235.1 |

OTHER PUBLICATIONS

International Search Report; PCT/NZ2014/000033; dated May 22, 2014, 7 pages.

* cited by examiner

HUMIDIFIER FOR A RESPIRATORY ASSISTANCE DEVICE, A RESPIRATORY ASSISTANCE DEVICE AND RELATED METHODS AND APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD

This invention relates to a humidifier for a respiratory assistance device, a respiratory assistance device comprising a humidifier and related methods and apparatus.

BACKGROUND

A respiratory assistance device typically comprises a housing provided with a blower or the like arranged to blow gas along a delivery conduit to a patient interface at the face of a patient. The patient interface may comprise a full or partial face mask, or a nasal cannula, for example. Gas, typically air or oxygen enriched air for example, is driven along the delivery conduit to the patient interface to increase the pressure in the airway of the patient. This can assist with the breathing of the patient, and may be used in treatment of sleep apnoea for example.

It can be desirable to control the humidity of the gas delivered to the patient and in that instance a humidifier may be provided, either as part of the respiratory assistance device, or elsewhere along the gas flow path. The humidifier typically comprises a chamber arranged to be filled or partially filled with a liquid, usually water, and a heating plate underneath the chamber. The water is vaporised by the heating plate, and the water vapour passes into the stream of gas being delivered to the patient to humidify the gas.

The use of an electric heating plate, or heating coil or the like, increases the energy consumption of the device. Such an arrangement is not typically able to react quickly to changes in the desired humidity since it is necessary to heat the entire body of water in the chamber to generate water vapor, also resulting in a lag between the humidifier being switched on, and water vapour being delivered to the gas stream. Furthermore such an arrangement is relatively unwieldy in terms of size, shape, and where it can be located. Yet further, the increased temperature inside the chamber means that the chamber walls must be configured to withstand such temperatures. There are also safety implications associated with a heated body of water.

In a paper entitled 'Solar Vapor Generation Enabled by Nanoparticles' published 19 Nov. 2012, the entire contents of which are incorporated by reference, Neumann, Urban, Day, Lal, Nordlander and Halas have described the generation of water vapours by illuminating metal or carbon nanoparticles dispersed in a body of water. Light energy is directed onto the nanoparticles which absorb the light energy and convert some of it to heat. The heated nanoparticles heat the water in the region around each particle, generating water vapour around each particle. The water vapour passes up through the body of water and is released as steam.

SUMMARY

It is an object of the invention to provide a humidifier and/or associated apparatus which overcomes or at least ameliorates one or more disadvantages of the prior art.

Alternatively, it is an object to provide a respiratory assistance device and/or associated apparatus which overcomes or at least ameliorates one or more disadvantages of the prior art.

Alternatively, it is an object to provide methodology which may assist in overcoming or ameliorating one or more disadvantages of the prior art.

Alternatively, it is an object to at least provide the public with a useful choice.

Further objects of the invention will become apparent from the following description.

Accordingly in one aspect the invention may broadly be said to consist in a humidifier for a respiratory assistance device, the humidifier comprising a chamber configured to contain liquid to be evaporated and metallic and/or carbon-based material, preferably in the form of nanoparticles, configured to be in contact with the liquid, the humidifier being configured such that, in use, at least a portion of the contents of the chamber are exposed to light such that light impinges on the metallic and/or carbon-based material to generate localised heating of liquid molecules around the metallic and/or carbon-based material and generate vapour for use by the respiratory assistance device. Although the metallic and/or carbon-based material may be nanoparticles, the disclosure is not limited to nano sized particles and other sizes of particles may be used, such as microparticles for example.

The metallic and/or carbon based nanoparticles are relatively high absorbers of optical radiation and therefore dramatically rise in temperature when subject to optical radiation. Some of this absorbed energy is re-radiated through light scattering, but it has been discovered that some of this absorbed energy is not re-radiated, resulting in an increase in temperature in the vicinity of the particle surface. Liquid adjacent the particle surface is subject to this absorbed energy which results in vapour forming around each nanoparticle. This vapour is released into the headspace in the chamber and delivered via a gas flow path to a patient.

A benefit of this process is that vapour is only formed in a vicinity closely localised to each nanoparticle. This, and the relatively large increase in temperature of each nanoparticle during light absorption, very quickly produces vapour localised closely to each nanoparticle resulting in the gas flow path being humidified relatively quickly. This also results in the liquid not localised to each nanoparticle not being heated significantly. Thus the main body of liquid may remain relatively cool, even during vapour generation.

The metallic and/or carbon-based material may simply be placed or fed into the chamber. Additionally or alternatively, the material may form part of a wall of the chamber or be coupled or affixed thereto. Preferably, the material is provided on a surface that contacts liquid in the chamber in use.

The humidifier may comprise a light source arranged such that the light from the light source is incident on the nanoparticles in the chamber, although an external light source may alternatively be used including natural light.

The humidifier may comprise a housing, the light source being provided in the housing, between the housing and the chamber.

The light source may comprise a laser or an LED for example. The colour of the emitted light may be arranged to be indicative of a status or operating condition of the humidifier. For example, the emitted light may be green when the humidifier is running and red when a fault is detected. In some embodiments, the light source may include light that is outside the visible spectrum, such as infrared and ultraviolet light.

One or more lenses may be associated with the light source so as to control distribution of light into or within the chamber. For example, one or more lenses may be placed between a light source and the chamber. Additionally or alternatively, at least a portion of a wall of the chamber may comprise a lens. Additionally or alternatively, one or more lenses may be provided inside the chamber and positioned with respect to a light source such that light generated thereby impinges thereon.

Similarly, one or more mirrors may be provided to control the path and/or distribution of light directed at the chamber. Mirror(s) may provide options as to the placement of the light source and/or re-direct light that does not impinge on the nanoparticles back into the chamber. For example, at least a portion of the inner walls of the chamber may be reflective such that light received in the chamber is reflected therearound. Additionally or alternatively, surfaces exterior to and opposing the exterior walls of the chamber may be reflective to perform the same task. For example, where a housing is provided, at least a portion of the inside of the housing may be reflective.

Preferably, any such reflective surfaces/walls are configured to concentrate light back towards the chamber. For example, the surfaces/walls may be arced or generally concave or incorporate concave portions, relative to a position inside the chamber.

Other optical means may be provided to manipulate light on its path from a light source. For example a diffractor (diffractive lens) or diffuser may be provided to scatter or disperse light from a light source such that the light is spread more widely throughout the chamber. In the case of the diffuser, a high-intensity light source may be used since the diffuser reduces the intensity of the light source. Further, optical fibres may be used to transmit light as desired to portions of the chamber. In another example, a multi-path optical system can be used to increase the heating area.

Broadly speaking, any such optical means (including lenses and reflectors/mirrors) may be provided at any point between a light source and the chamber contents, including in a wall of the chamber and internal or external to the chamber. Note that the relative placement of optical means between the light source and the chamber contents is with reference to the path of the light and not limited by reference to actual relative physical placement of the chamber and light source. For example, a light source may be arranged to direct light away from the chamber onto a concave mirror from where it is directed towards the chamber.

The chamber may have at least one light transporting or transparent portion, that is, a portion that allows the transport of light therethrough so that light from the light source is able to impinge on the chamber contents to generate vapour. In one embodiment, the chamber comprises a substantially transparent side wall portion and/or a substantially transparent base portion. For the avoidance of doubt, when used herein, "portion" may be interpreted as including a whole of the article to which it refers, as well as any part thereof. For example, the "substantially transparent base portion" may be interpreted as an entire base being substantially transparent.

The light transporting portion may selectively allow for light transport therethrough. For example, the portion may comprise a one-way mirror that substantially allows light to be transported therethrough in a first direction (i.e., from the light source to the chamber) but substantially not in the opposite direction (i.e., out of the chamber).

Where a portion of the chamber is light transportable or transparent, ambient light external thereto may affect vapour generation within the chamber. Consequently, light shielding or blocking portions may be provided to better control light able to enter the chamber. For example, when provided, the housing may, at least to some degree prevent light entering the chamber to prevent fluctuations in the amount of vapour generated due to fluctuations in the level of ambient light. Additionally or alternatively, a portion of the chamber wall or a shielding element external thereto may comprise one or more filters to block transport therethrough of light having a particular wavelength or frequency, or particular range(s) of wavelengths or frequencies.

The humidifier may further comprise a mixer or agitator arranged to improve dispersion of the nanoparticles within the liquid. For example, a rotatable mixing arm or blade may be provided in the chamber to mix the nanoparticles and liquid before and/or during vaporisation. Additionally or alternatively, vibrations may be imparted to the chamber.

An electric field may be generated in the chamber to control movement of the nanoparticles. A pair of conducting surfaces with a bias voltage can be placed on opposite sides of the chamber such that polarity may be changed and the field strength may be altered to move the charged particles from a "source" location to a "collection" point at varying speeds, with the option of changing directions of movement by changing the polarities of the conducting surfaces.

Additionally or alternatively, a magnetic field may be generated within the chamber to control movement of the nanoparticles. Thus, one or more coils of conducting wire may be provided in or outside the chamber wall and coupled to an electrical power supply. Control electronics can be used to control the direction of flux of the resultant field which in turn can be used to control the position of the nanoparticles. Preferably, at least two coils are provided to control movement therebetween. Such a configuration may enable the particles to remain in suspension within the heated liquid and/or may also be used to control particle distribution and density within the liquid and/or to alter the position of clusters within an optical path from the light source.

Additionally or alternatively, a member having predetermined electrostatic properties may act as a barrier or otherwise control movement of the metallic and/or carbon-based material. For example, a grid may be provided proximate the outlet that electrostatically repels the material. Additionally or alternatively a grid or a portion of the base of the chamber may electrostatically attract the material.

The humidifier preferably comprises an inlet configured to allow gas to enter the chamber.

Preferably, the inlet is positioned in the roof or an upper sidewall of the chamber, above the level of liquid in the chamber in normal use.

Preferably, the inlet is configured to receive gas with a pressure elevated above atmospheric pressure.

According to one embodiment the inlet, or an additional inlet coupled to the pressurised gas supply, is provided below the normal water level so as to agitate the chamber contents in use.

Preferably, the chamber comprises an outlet to enable vapour to exit the chamber.

Preferably, the outlet is positioned in the roof or an upper sidewall of the chamber, above the level of liquid in the chamber in normal use.

Thus, gas may enter the chamber, be humidified by vapour generated therein, and then exit through the outlet for subsequent delivery to a patient, albeit typically via one or more conduits and a patient interface or mask.

The chamber may comprise a single substantially singular wall without the need for any seals at its base, which has generally been required in the past where a chamber sits on a heatplate. This may reduce the cost of the chamber. For example, the chamber may be formed from a moulding process with all walls thereof formed from the same material. Preferably, the material is a plastic.

The chamber may comprise a material having relatively low heat resistant and conductive properties because the chamber does not need to cope with a body of hot liquid as the bulk of the liquid remains relatively cool during the humidification process and it is not necessary for heat to be transferred through a wall thereof.

A nanoparticle retention device may be provided and operative to retain the nanoparticles in or adjacent the chamber such that nanoparticles do not pass to the patient interface, that is, the nanoparticles are restricted from being inhaled by the patient. The retention device may comprise an electromagnetic device arranged to generate an electromagnetic field which attracts or repels the nanoparticles. For example, the coils described above with regards agitation may additionally or alternatively be configured to retain the nanoparticles inside the chamber. In another example, the retention device may comprise a filter arranged to allow the humidified gas stream to pass therethrough but to block the nanoparticles.

According to a second aspect, the invention may broadly be said to consist in a respiratory assistance device comprising a gas flow conduit adapted to be located in use between a source of supply gas and a patient interface to define a gas flow path therebetween, the device further comprising a humidifier comprising a chamber configured to contain liquid to be evaporated and metallic and/or carbon-based material, preferably in the form of nanoparticles, the humidifier being configured such that, in use, the contents of the chamber are exposed to light such that light impinges on the nanoparticles to generate localised heating of liquid molecules in the chamber and generate vapour, the vapour being delivered to the gas flow conduit to humidify gas therein.

Preferably the device comprises a controller operative to control the amount of water vapour generated and therefore the humidity of the gas in the gas flow path. The controller may be microprocessor based and may include a memory on which a controlling algorithm is stored. The controller may be arranged to control the amount of water vapour generated automatically, or on the basis of an operator input.

The controller may be arranged to control the amount of water vapour generated by controlling the amount of light incident on the chamber. In one example, the light source itself is controlled. In another example, the path of the emitted light between the light source and the chamber may be controlled, for example by blocking or partially blocking the light path, or by using suitable filters in the light path. Alternatively or additionally, the light transmitting characteristics of the chamber itself may be varied to control the amount of light that passes into the chamber. For example, the transparency and/or reflectivity of the chamber may be controlled.

A heater may be provided in the gas flow path arranged to heat the gas prior to humidification enrichment. For example, a heater wire may be provided in, along or around part of the gas flow path, or a heated cuff provided around part of the gas flow path.

The controller may be arranged to control the amount of water vapour generated by varying the light impinging on the metallic and/or carbon-based material with the heater controlled to prevent condensation of vapour generated. Thus, in one example, the heater is controlled to heat the gas substantially to or greater than a dew point temperature of the liquid. In heating the gas, the controller may take account for any heat added within the chamber including by light impinging on the metallic and/or carbon-based material, such that the heater heats the gas to a lower temperature (e.g., below the dew point temperature) but rises in temperature to above the threshold inside the chamber headspace.

A light source may be provided, on the device or the humidifier, and arranged such that the light from the light source is incident on the nanoparticles in the chamber.

The humidifier may comprise a housing, the light source being provided in the housing, between the housing and the chamber.

The light source may comprise a laser or an LED for example. The colour of the emitted light may be arranged to be indicative of a status or operating condition of the humidifier. For example, the emitted light may be green when the humidifier is running and red when a fault is detected. In some embodiments, the light source may include light that is outside the visible spectrum, such as infrared and ultraviolet light.

The humidifier preferably comprises a gas vapour outlet arranged to be fluidly coupled to a pressurised gas supply.

A lens may be provided between the light source and the chamber to control the distribution of light into the chamber.

A mirror may be provided at the chamber to assist in reflecting light from the light source into the chamber. Additionally or alternatively, at least part of the interior walls of the chamber may be reflective to retain light inside the chamber once received. Additionally or alternatively, surfaces exterior to and opposing the exterior walls of the chamber may be reflective to perform the same task. Such surfaces/walls may be configured to concentrate light back towards the chamber. For example the surfaces/walls may be arced or generally concave or incorporate concave portions.

Other optical means may be provided at the chamber as required, to manipulate the light from the light source. For example a diffractor or diffuser may be provided positioned between the light source and the chamber, to scatter or disperse the light from the light source such that the light is spread more widely throughout the chamber. In the case of the diffuser, a high-intensity light source may be used since the diffuser reduces the intensity of the light source. In another example, a multi-path optical system can be used to increase the heating area.

A fibre optic cable may be arranged to deliver light from the light source to the chamber. More than one fibre optic cable may be provided for this purpose.

The chamber may have at least one light transmitting portion, that is, a portion that allows transmission of light from the light source, through that portion of the chamber. In one embodiment, the chamber comprises transparent side walls and/or a transparent base.

A mixer or agitator may be provided arranged to improve dispersion of the nanoparticles within the fluid. For example, a rotatable mixing arm or blade may be provided in the chamber to mix the nanoparticles and fluid before and/or during vaporisation.

A nanoparticle retention device may be provided and operative to retain the nanoparticles in or adjacent the chamber such that nanoparticles do not pass to the patient interface, that is, the nanoparticles are restricted from being inhaled by the patient. The retention device may comprise an electromagnetic device arranged to generate an electric field which attracts or repels the nanoparticles. In another example, the retention device may comprise a filter arranged to pass water vapour but to block nanoparticles.

Again, a heater may be provided in the gas flow path arranged to heat the gas prior to humidification enrichment. For example, a heater wire may be provided in, along or around part of the gas flow path, or a heated cuff provided around part of the gas flow path.

The controller may be arranged to control the amount of water vapour generated by controlling the heater and may further control the heater to prevent condensation. In one example the heater is controlled to the chamber headspace is above the dew point temperature of the liquid. In heating the gas, the controller may take account for any heat added by the chamber.

A gas heater may be provided in the gas flow path arranged to heat the gas after humidification enrichment. This may assist in alleviating condensation in the gas flow path between the humidifier and the patient outlet.

More particularly, preferably the respiratory assistance device of the second aspect comprises a humidifier of the first aspect.

According to a third aspect, the invention may broadly be said to consist in a humidification apparatus for a respiratory assistance device, the apparatus comprising:

a first conduit and a second conduit, wherein the first and second conduits are generally coaxially arranged, wherein at least a portion of a wall bordering between the first and second conduits allows vapour, preferably water vapour, to pass from the first conduit to the second conduit but substantially prevents liquid, preferably water, passing therethrough, wherein the first conduit contains and/or at least a portion of a wall thereof comprises metallic and/or carbon based material, preferably in the form of nanoparticles, and wherein the apparatus is configured such that in use, light impinges on the metallic and/or carbon-based material to generate vapour and/or heat.

Preferably, the first conduit is located inside the second conduit but the converse is also possible.

According to one embodiment, at least one light source is provided inside the first conduit to generate said light.

Additionally or alternatively, other light source(s) may be provided, including external to said first and or said second conduit, with walls being light transparent or transmissible as required.

According to a preferred embodiment, light is generated by at least one optical fibre that is preferably provided inside the first conduit.

Again, light impinging on the metallic and/or carbon-based material may be controlled by controlling the optical properties of walls of the conduits and/or a housing or sheath therearound, including providing transparent and/or light blocking and/or light reflective portions.

According to another aspect, more conventional electrical resistance type heating means are provided in place of the metallic and/or carbon-based material and light combination of the apparatus of the third aspect. More particularly, for example, an inner conduit surrounds or comprises (e.g. in at least a portion of a wall thereof), at least one electrical resistance wire. Liquid is fed into the inner conduit and heated as it passes therethrough, generating vapour. By forming at least portion of the wall of the inner conduit from a material that allows vapours to pass therethrough, vapour may pass into an outer conduit, arranged coaxially with the inner conduit which is arranged substantially coaxially with the inner conduit. The gas supply is fed to the outer conduit, resulting in humidification thereof.

The arrangements of the third and alternative third aspect mean that a conventional humidifier is no longer required, with the humidification capable of being provided simply in a conduit positioned between the pressurised gas supply and the patient interface.

According to a fourth aspect, the invention provides a heater for a respiratory assistance device, the heater comprising:

a body; and metallic and/or carbon based material, preferably in the form of nanoparticles, wherein the metallic and/or carbon based material is integral to or coupled to the body and configured to receive light in use, and wherein at least one surface of the body is configured to come into contact (or at least be in close proximity to) a fluid used by the respiratory assistance device, in use, whereby light incident on said metallic and/or carbon based material heats said fluid.

Preferably, the material is provided at or near said at least one surface to improve heating resulting therefrom.

The fluid may comprise but is not limited to air and may be humidified and/or oxygen enriched as required.

The body may form a conduit such that the fluid passes therethrough. For example, the body may form at a least a part of the conduit connecting the humidifier to the gas supply and/or the humidifier to a patient interface.

According to one embodiment, a light source is provided inside the body.

Preferably, the light source comprises one or more optical fibres.

One or more optical fibres may be positioned inside the body and configured to emit light therein.

Where the light source is provided inside the body, the body may prevent light external to the body impinging on the metallic and/or carbon based material so as to provide better control of the level of heating by preventing heating caused by ambient light.

According to another embodiment, a light source is provided external to the body.

According to another embodiment, the body is provided in a housing with a light source provided between the body and the housing. Conveniently, the housing and the body may be in the form of substantially hollow members with the body positioned inside the housing, preferably substantially coaxially.

According to another embodiment, the body forms an element that is insertable inside the chamber and is used to heat and/or generate vapour from liquid therein.

According to a fifth aspect, the invention may broadly be said to consist in humidification fluid for a respiratory assistance device, the fluid comprising a liquid and metallic and/or carbon based nanoparticles.

According to a sixth aspect, the invention may broadly be said to consist in a supplement for liquid used for humidification in a respiratory assistance device, the supplement comprising metallic and/or carbon based nanoparticles.

According to a seventh aspect, the invention may broadly be said to consist in a refill for a humidifier for use with a respiratory assistance device, the refill comprising a chamber for mounting on the humidifier, the chamber containing at least one of:

a liquid; and metallic and/or carbon based nanoparticles.

Preferably, where only one of the liquid and the metallic and/or carbon based particles are provided inside the chamber, the chamber is configured to enable the other constituent to be added.

According to an eighth aspect, there is provided a method of generating heat and/or vapour for providing respiratory assistance, the method comprising at least one of:

providing a humidification fluid containing metallic and/or carbon-based material;

providing a humidification chamber and/or heater element and/or conduit comprising metallic and/or carbon-based material;

subjecting metallic and/or carbon-based material to light so as to generate heat and/or vapour for use in respiratory assistance care.

Other aspects of methods of the invention may be derived from the apparatus aspects above and the description that follows.

For all aspects, preferably the humidification liquid is water or predominantly water and the gas is air or oxygen enriched air. However, the invention is not limited thereto. For example, drugs may be added to the chamber such that they are delivered to a patient in use. Alternatively, particularly during a cleaning cycle, a cleaning fluid may be provided in the chamber.

It should be noted that aspects of the invention may be used in combination. For example, the humidifier of the first aspect may be used in combination with the apparatus of the third aspect.

Further aspects of the invention, which should be considered in all its novel aspects, will become apparent from the following description.

DRAWING DESCRIPTION

A number of embodiments of the invention will now be described by way of example with reference to the drawings in which.

DETAILED DESCRIPTION OF THE DRAWINGS

Figure 1:
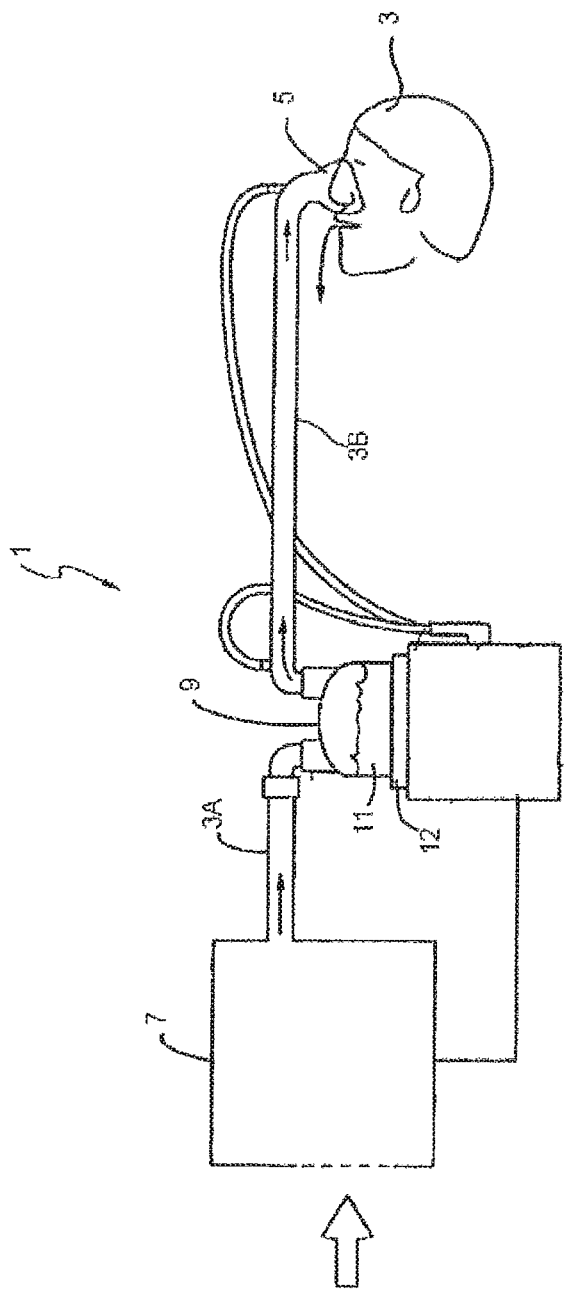
FIG. 1 is a schematic of a prior art respiratory assistance device incorporating a humidifier.

Throughout the description like reference numerals will be used to refer to like features in different embodiments.

The humidifier in accordance with the present invention may be used with any respiratory assistance device, or as part of any respiratory assistance system, where a gas stream requires humidification enrichment.

An example respiratory assistance system can be seen in FIG. 1 and comprises a humidifier. The system is a humidified Continuous Positive Airway Pressure (CPAP) system 1 which provides humidified and pressurised gas to a patient 3 via a patient interface 5 which in this example comprises a nasal mask. Supply gas is provided by a blower arrangement 7, via a gas delivery conduit 3A to a humidifier 9 comprising a chamber 11 filled with a liquid to be evaporated. The humidifier 9 comprises a heating plate 12 or heating coil or the like, generally below the chamber 11. The vapour generated passes from the chamber 11 into the gas flow path via gas delivery conduit 3B connected to the patient interface 5.

While the invention is described below in relation to this system, it will be appreciated that the humidifier in accordance with the present invention may be used with any type of respiratory assistance system, including, for example, a Variable Positive Airway Pressure (VPAP) system or a Bi Level Positive Airway Pressure (BiPAP) system. Further, alternative means may be provided for generating the gas stream and/or for transporting the stream from the humidifier chamber to the patient i.e., alternative conduit and/or patient interface arrangements may be used. Those skilled in the art would be familiar with selecting different, known components to build the system for a particular implementation based on a patient's diagnosis and preferences, as well as due to cost and technical constraints.

Figure 2:
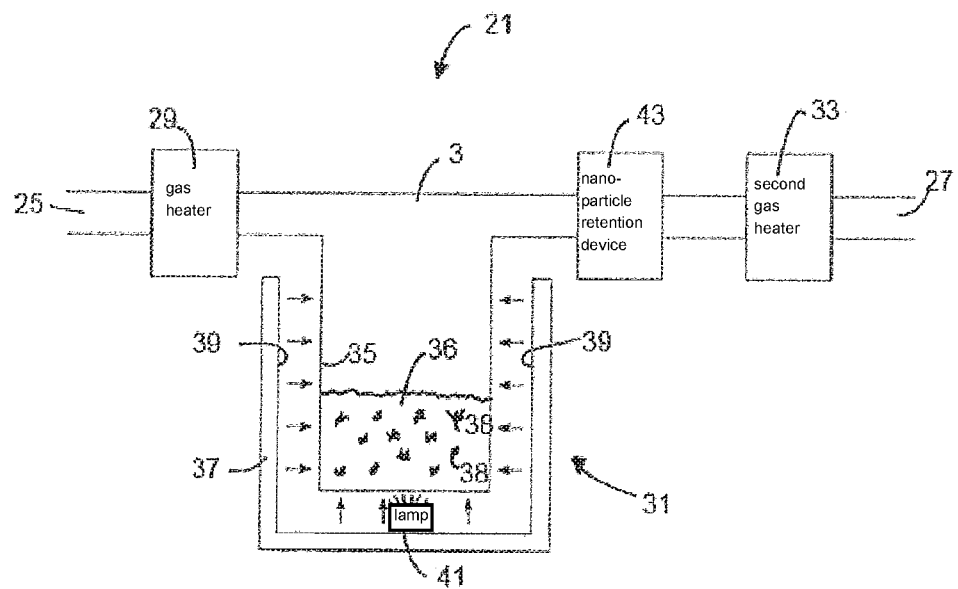
FIG. 2 is a schematic side view of a first embodiment of a respiratory assistance device and humidifier in accordance with the invention.

Referring to FIG. 2, part 21 of a respiratory assistance device according to an embodiment of the invention is shown. The respiratory assistance device comprises a gas flow path in the form of a gas delivery conduit 3 (which includes the headspace in the shown chamber) having an inlet 25 to receive gas from a source of supply gas (not shown) and an outlet 27 to deliver gas to a patient interface (not shown). The patient interface may, for example, comprise a full or partial face mask or a nasal cannula. The supply gas is driven along the gas flow path 3 and delivered to the patient to pressurise the patient's airway. For example, blower arrangement 7 of FIG. 1 may be configured to couple to inlet 25, and conduit 3B and nasal mask 5 of FIG. 1 may be configured to couple to outlet 27.

An optional gas heater 29 is provided to preheat the supply gas prior to entering the gas flow path. As noted hereinbefore, the novel humidifier of the invention provides more localised heating of a portion of the liquid inside the humidifier chamber and as such, additional heating may be required of the gas stream to prevent or reduce condensation being generated within the chamber or shortly after exiting the chamber. Conduits including heater elements are known in the art and may, for example, include a heater coil of resistance wire incorporated into the wall of the conduit.

The humidifier 31 is provided downstream of the gas heater 29, and upstream of a second optional gas heater 33 arranged to maintain the temperature of the gas after being humidified by the humidifier 31. The second optional gas heater 33 may be configured in a similar manner to the first optional gas heater.

The humidifier 31 is arranged to provide vapour, which may be but is not limited to water vapour, to the gas stream in the gas flow path 3, prior to delivery of the gas to the patient. The vapour is generated via a nanoparticle based heating arrangement. In particular, the humidifier 31 comprises a chamber 35 containing humidification liquid 36, typically water, and metallic and/or carbon based nanoparticles indicated schematically of 38. The nanoparticles are subject, in use, to light which may be ambient light, or light from an artificial light source. At least a portion of the contents of the chamber are exposed to light such that light impinges on the nanoparticles to generate localised heating of liquid molecules in the chamber and generate vapour for use by the respiratory assistance device.

The energy of the received light heats the nanoparticles to a relatively high temperature, preferably to or above the boiling point of the liquid. This heat vaporises the liquid in a region surrounding each nanoparticle. The vapour rises and passes from the chamber 35 into the gas stream in the gas flow path 3. The process continues until the light source is removed.

In this example, the chamber 35 is generally cylindrical. The chamber 35 may be pre-charged with liquid and/or nanoparticles prior to mounting the chamber on or in the humidifier 31, or these may be added subsequently. The chamber 35 and/or humidifier 31 may be removably mounted on a part of the respiratory assistance system.

The chamber 35 may be mounted within an outer housing 37, the inner walls 39 of which may be light reflective. In the illustrated embodiment, a light source is provided in the form of a lamp 41 located at the base of the chamber 35 in the void between the chamber 35 and the outer housing 37. The light from the light source 41 is incident on the base and side walls of the chamber 35 as indicated by the arrows 42. The reflective inner walls 39 assist in delivering the light to the chamber 35. It will be appreciated that the light source may be positioned elsewhere and/or more than one light source may be provided, the intensity or number of which in use may be varied depending on the required level of humidification.

In this example, the walls of the chamber 35 are sufficiently transparent that the light from the light source 41 passes through the walls 39 of the chamber 35 and is incident on the nanoparticles and liquid contained in the chamber 35. This initiates fluid vapour generation via the light heating the nanoparticles, as described above. The generated vapour passes from the chamber 35 into the gas stream 3 and humidifies the gas prior to delivery to the patient. The second gas heater 33 is arranged to heat the humidified gas to reduce or alleviate condensation along the path to the patient interface.

In an alternative arrangement, the light source may be positioned inside the chamber 35, including being positioned in a wall thereof. While housing 39 may still be constructed as shown in FIG. 2, alternatively, the walls of the chamber 35 may be reflective.

According to a yet further alternative, a light source may be configured external to the chamber 35 so as to direct at least a portion of the light emitted thereby through a light transmissible portion of the chamber 35 wall. At least some of the remainder of the wall of the chamber 35 may be reflective to retain light inside the chamber.

According to some embodiments, the light source(s) are configured to emit pulsed light with the ratio of ON:OFF times preferably being adjustable to control the level of humidification. Such ratios may be predetermined based on experimental data. Alternatively, the humidity inside and/or downstream of the chamber may be monitored and used to control the light source accordingly e.g. a longer ON time and/or shorter OFF time may be used if increased humidity is required.

A nanoparticle retention device 43 is provided in the gas flow path 3, downstream of the humidifier chamber 35. The device 43 is arranged to prevent nanoparticles in the gas stream from passing through the device 43 and into the patient interface and the patient airway.

The device 43 may be electromagnetic and arranged to generate an electro-magnetic field that attracts or repels the nanoparticles. Alternatively or additionally, the device 43 may incorporate a barrier or filter arranged to allow vapour to pass, but retain the nanoparticles. The device 43 may alternatively be positioned at or adjacent the outlet of the chamber, or within the chamber.

A wide variety of types of light source may be used such as an LED or LED cluster for example. The light source need not be located at the chamber 35 and could be remote therefrom. In that instance the light may be delivered to the chamber 35 via a fibreoptic cable or cables for example.

The light source may be external to the outer housing 37 and may comprise ambient light. In that instance the outer housing 37 of the humidifier 31 may be arranged to allow light to reach the chamber 35. In such embodiments, at least a portion of the wall of the housing 37 may substantially prevent or selectively substantially prevent light from entering the housing 37 so as to prevent the generation of vapours when not required.

The nanoparticle heating arrangement generates vapour relatively quickly due to the rapid increase in temperature of the nanoparticles when subject to light, and also due to the side effect that the vapour is generated only in close proximity to each nanoparticle. Thus, the bulk of the body of the liquid may not be heated, or at least not heated significantly, heating being localised to the nanoparticles. This reduces the energy consumption of the humidifier 31 as compared to using a standard heating plate or heating coil. This effect also lessens the material requirements of the chamber 35, allowing a material to be selected that need not be capable of withstanding the relatively high temperatures of prior art humidifiers. Further, many existing chambers include a metallic base plate to assist in heat transfer from the heater plate positioned thereunder in use. The present invention enables the complete chamber to be formed from plastics, for example, simplifying and reducing the cost of production.

The humidifier of the invention provides greater and more rapid control of the amount of vapour generated, and therefore the humidity of the gas supplied to the patient since it can be changed relatively quickly, and repeatedly, allowing the humidity level in the gas stream to be accurately tailored and/or varied to the patient's varying needs by changing characteristics of the light source(s) (e.g. intensity or brightness, "ON time", number of light sources used) and/or by adjusting the path of the light generated thereby (e.g. using mirrors or light blocks or other optical means to control whether and/or how much light is directed at the chamber 35 contents and/or whether and/or to what extent that light is retained inside the chamber 35).

A further benefit is that the fluid consumption may be reduced, as the vapour generated is more precisely controlled as compared to a prior art humidifier since the lags associated with heating a larger body of water are not present, at least to the same degree, in arrangements incorporating the invention.

The above therefore provides an improved humidifier for a respiratory assistance device which uses nanoparticles to generate localised heat, and therefore localised vapour for humidifying enrichment of a gas stream.

The humidifier 31 may be arranged to be mounted on an existing respiratory assistance device in place of a prior art humidifier. The humidifier 31 comprises the components necessary to generate vapour and deliver the vapour into the gas flow path. The humidifier 31 therefore comprises at least the chamber 35 and connections between the chamber 35 and the gas flow path 3. The humidifier 31 may comprise an integral light source, and a power connection for connection to an electrical power source which may be integral or couplable to the respiratory assistance device.

The liquid to be evaporated and the nanoparticles may be supplied as a humidification fluid comprising a pre-mixture of predetermined amounts of liquid and nano-particles. The chamber 35 may be filled, or refilled, prior to each use. Alternatively the chamber 35 may be supplied prefilled with a humidification liquid. Once used, the chamber 35 may be removed from the humidifier 35 and replaced. Alternatively, a user may fill the chamber 35 with a requisite amount of liquid and then add nano-particles thereto. This process may be reversed. Note that the nanoparticles may be re-used and a liquid such as water simply added to the chamber, as required.

Figure 3:
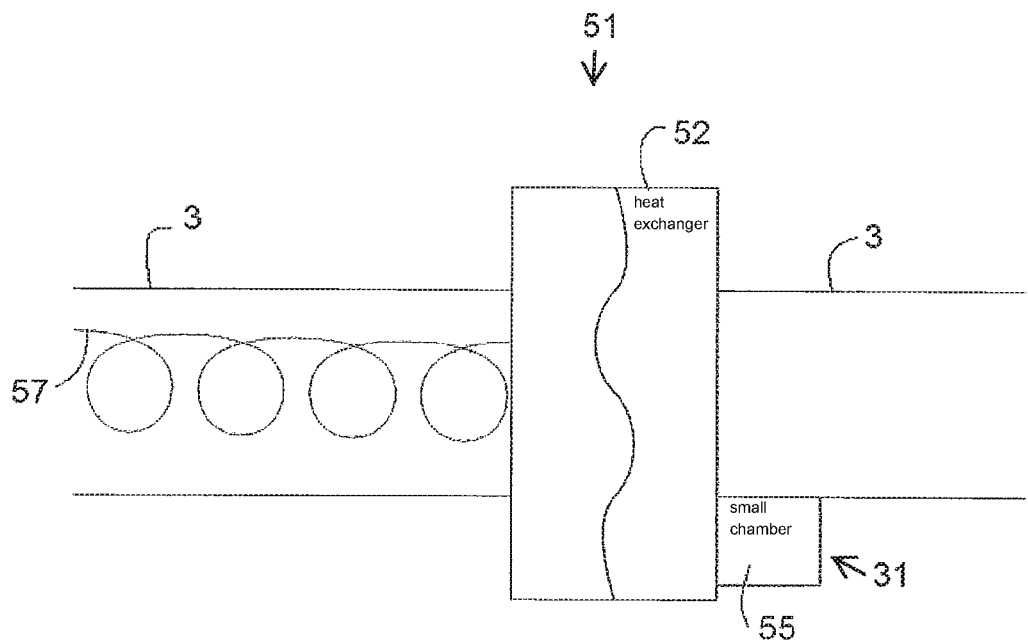
FIG. 3 is a schematic side view of a second embodiment of a respiratory assistance device and humidifier in accordance with the invention.
Figure 4:
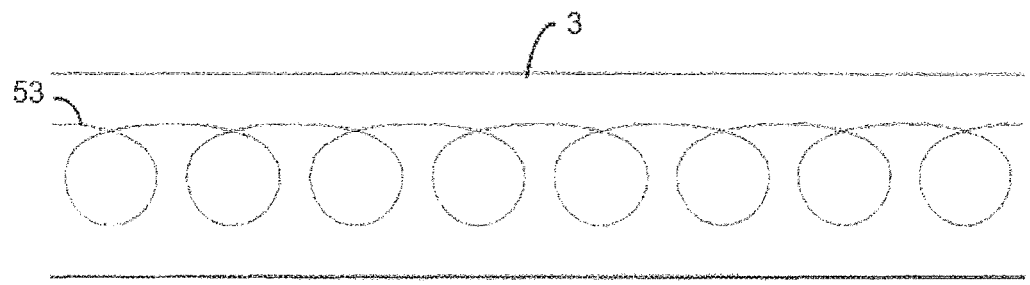
FIG. 4 is a schematic side view of a third embodiment of a respiratory assistance device in accordance with the invention.
Figure 5:
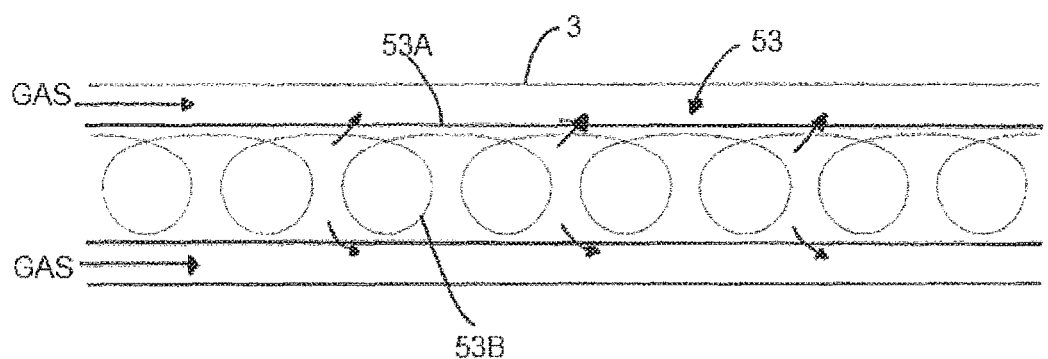
FIG. 5 is a schematic side view of a third embodiment of a respiratory assistance device and humidifier in accordance with the invention.

Referring to FIG. 3, an alternative humidification part 51 of a respiratory assistance device is shown comprising a gas flow path in the form of a delivery conduit 3. In this example, a gas heat exchanger 52 is provided between the source of supply gas and the patient interface. The heat exchanger 52 is arranged to transfer heat to/from the supply gas to the patient, and the expiratory gas from the patient in use.

In this example, the humidifier 31 comprises a relatively small chamber 55 adjacent the heat exchanger 52 and adjacent the patient interface (not shown), that is, at the patient end of the gas flow path 3.

A light source is provided remotely and light delivered along a fibre optic cable 57 which extends inside the delivery conduit 3 to the heat exchanger 52. The light is delivered by the fibre optic cable 57 to the small chamber 55 to generate vapour as described above.

Optionally, the delivery conduit 3, or the outer material of the fibre optic cable 57, or an intermediate coaxial tube (not shown), may be provided with nanoparticles which are subject to light from the fibre optic cable 57, or from a further light source, to generate heat as well as, or alternatively to, generating vapour for humidification. This heat can be used in the heat exchanger 52 to heat the supply gas prior to delivery to the patient. The nanoparticles may be embedded in the material of the delivery conduit 3, the fibre optic cable 57 or in part of the heat exchanger 52, light being delivered as required to the location of the nanoparticles. Thus, it is envisaged that heating from nanoparticles could be used instead of, or to supplement, a more common resistance wire type electrical heating arrangement. Eliminating the need for resistance wire type heaters can be particularly useful in some hospital environments to reduce the emission of electromagnetic radiation which may interfere with some equipment. For example, during a medical scan such as a MRI scan. Alternatively they may be of value where a suitable electrical power source is not locally available. Yet further, such embodiments can provide for improved safety by removing the need for electrically conducting wires, at least in the region of the vapours.

In a modification of the above, liquid may be supplied to the patient, using capillary action, from a centralised or remote fluid source, whereby liquid is drawn from a reservoir as it is used.

Referring to FIG. 4, a combined heating and humidifying tube comprises a gas delivery conduit 3 inside of which is provided a heating/light tube 53. The supply gas flows along the delivery conduit 3, outside the heating/light tube 53. Liquid contained in the tube 53 is heated via light incident on nanoparticles also in tube 53 to generate vapour which passes from the tube 53 into the gas delivery conduit 3. Thus, the walls of the tube 53 are preferably permeable to evaporated liquid (i.e., allow at least a portion of the vapours to pass from inside the tube 53 to the gas stream in conduit 3) but preferably substantially inhibits liquid from passing through the wall of the tube 53. The material of the tube 53 may comprise a Sympatex® or similar material for example.

Referring to FIG. 5, a modified heating light tube 53 is of coaxial form comprising an outer tube 53A, and inside of which is provided a fibre optic cable 53B through which light passes. Fluid and nanoparticles are provided inside the outer tube 53A but outside the fibre optic cable 53B. The material of the outer tube 53A is chosen to allow evaporated liquid to pass through the wall of the outer tube 53A and into the gas stream in the delivery conduit 3, but to retain the nanoparticles and liquid within the outer tube 53A. The material of the outer tube 53A may comprise a sheath of a Sympatex® or similar material for example. The fibre optic cable 53B comprises at least one light delivery device arranged to transmit the light from the fibre optic cable into the tube 53. The light delivery device may comprise a ridge or the like including other surface contouring which causes light to exit the fibre optic cable 53B and heat the nanoparticles in the outer tube 53A. The liquid may be transported along the outer tube 53A by capillary action or via a powered pumping arrangement.

The gas delivery conduit 3 and the outer tube 53A may be sufficiently transparent to allow ambient or external light to pass into the outer tube 53A to heat the nanoparticles. The device may then be used in an unpowered mode for transportation or at another time where use of electrical power may not be possible, safe, available or practical. Alternatively, at least a portion of the conduit 3 and/or the outer tube 53A may substantially inhibit light passing therethrough so as to provide for greater control by removing variations in light level caused by changes in the level of ambient light.

The nanoparticles may be arranged to provide heat as well as humidity. The nanoparticles could therefore be embedded into the wall of the delivery conduit 3 and/or the outer tube 53A.

With continued reference to FIGS. 2 and 3, the nanoparticle retention device 43 may be provided with a filter of a barrier material such as Sympatex® material. Such a material has a porous structure with pores sized to allow liquid vapour to pass/diffuse into the supply gas path, but to block the nanoparticles. Such a material can be used in any other part of the humidifier 31 or respiratory devices 21, 51 where it is desired to separate the nanoparticles from the stream supplied to the patient.

An electric field may be used to control the dispersion and circulation of the nanoparticles within the liquid, and may be used as the primary method of retention of the nanoparticles within the evaporative system.

Whilst it is envisaged that suitable parts of the humidifier 33 may be sufficiently transparent that light can be transmitted through those parts into the fluid to be heated, it may alternatively be desirable to make such parts non-light transmitting in order to avoid any unwanted heating of the fluid due to external or ambient light. For example, if a co-axial type tube is used, the inner sheath may be formed from a non-transparent material.

Where it is desired to use the heating effect of nanoparticles to generate heat otherwise than for controlling humidification of the supply gas, the nanoparticles may be embedded into part of the material of the device, such that when subject to light, heat is generated to heat the material. For example, the nanoparticles may be embedded in the walls of the gas delivery tube 3, or one or both tubes of a coaxial tube.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

What is claimed is:

1. A humidifier for a respiratory assistance device, the humidifier comprising:
    a chamber configured to contain liquid to be evaporated,
    a metallic or carbon-based material configured to be in contact with the liquid,
    a mixer or agitator,
    an electric or magnetic field generator configured to generate an electric or magnetic field inside the chamber so as to control movement or positioning or speed of the metallic or carbon-based material,
    wherein the humidifier is configured such that, in use, at least a portion of an inside of the chamber is exposed to light such that light impinges on the metallic or carbon-based material to generate localised heating of liquid molecules around the metallic or carbon-based material and generate vapour for use by the respiratory assistance device.

2. The humidifier of claim 1, comprising an inlet configured to allow gas to enter the chamber.

3. The humidifier of claim 2, wherein the inlet is configured to receive gas with a pressure elevated above atmospheric pressure.

4. The humidifier of claim 1, comprising an outlet to enable vapour to exit the chamber.

5. The humidifier of claim 1, wherein walls forming the chamber are integrally formed as a singular article.

6. The humidifier of claim 1, comprising a nanoparticle retention device operative to retain nanoparticles in the chamber.

7. A respiratory assistance device comprising a gas flow conduit adapted to be located in use between a source of supply gas and a patient interface to define a gas flow path therebetween, the device further comprising a humidifier as set forth in claim 1.

8. The respiratory assistance device of claim 7, comprising a controller operative to control the amount of water vapour generated and therefore the humidity of the gas in the gas flow path.

9. The respiratory assistance device of claim 7, comprising a heater provided in the gas flow path arranged to heat the gas prior to humidification enrichment.

10. The respiratory assistance device of claim 7, comprising a heater provided in the gas flow path arranged to heat the gas before or after humidification enrichment.

11. The humidifier of claim 1, wherein said metallic or carbon-based material comprises a material that is carbon-based.

12. The humidifier of claim 1, wherein said metallic or carbon-based material comprises a metallic material.

13. The humidifier of claim 1, comprising a pair of conducting surfaces positioned on opposing regions of the chamber, wherein a bias voltage is configured to be introduced across the pair of conducting surfaces.

14. The humidifier of claim 1, wherein a bias voltage is configured to be introduced on opposing regions of the chamber such that polarity may be changed and the field strength may be altered.

15. The humidifier of claim 14, wherein the polarity is configured to control the direction of movement of particles.

16. The humidifier of claim 1, further comprising one or more coils disposed on opposing regions of the chamber.

17. The humidifier of claim 16, further comprising a controller in electronic communication with a power source, wherein the power source is configured to supply current to the one or more coils to generate a flux.

18. The humidifier of claim 17, wherein the controller is configured to control the power source to control the direction of the flux.

19. The humidifier of claim 1, further comprising a nanoparticle retention device operative to retain nanoparticles in or adjacent to the chamber such that the nanoparticles do not pass a patient interface.

20. The humidifier of claim 19, wherein the nanoparticle retention device comprises an electromagnetic device arranged to generate an electric field which attracts or repels nanoparticles.

* * * * *